United States Patent
Schilowitz et al.

(10) Patent No.: US 7,765,854 B2
(45) Date of Patent: Aug. 3, 2010

(54) MICROCANTILEVER STRESS SENSOR FOR FLUID ANALYSIS

(75) Inventors: Alan Mark Schilowitz, Highland Park, NJ (US); Dalia G. Yablon, Livingston, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 11/261,050

(22) Filed: Oct. 28, 2005

(65) Prior Publication Data

US 2006/0230817 A1    Oct. 19, 2006

Related U.S. Application Data

(60) Provisional application No. 60/628,282, filed on Nov. 16, 2004.

(51) Int. Cl.
*G01N 33/50* (2006.01)

(52) U.S. Cl. .................. 73/64.53; 73/53.01; 73/61.41; 436/518

(58) Field of Classification Search ............ 73/53.01, 73/61.41, 61.61, 64.41, 64.56; 436/518, 436/528, 3, 80, 111, 119, 120, 149, 151, 436/73

See application file for complete search history.

(56) References Cited

U.S. PATENT DOCUMENTS

| | | | |
|---|---|---|---|
| 5,807,758 A * | 9/1998 | Lee et al. ................... 436/526 |
| 6,016,686 A * | 1/2000 | Thundat ...................... 73/23.2 |
| 6,290,838 B1 * | 9/2001 | Mifsud et al. ............... 205/775 |
| 6,575,020 B1 * | 6/2003 | de Charmoy Grey et al. ........................ 73/54.23 |
| 6,773,926 B1 * | 8/2004 | Freund et al. ............... 436/149 |
| 2002/0045277 A1 * | 4/2002 | Schmid et al. .............. 436/518 |
| 2002/0072127 A1 * | 6/2002 | Sofield et al. ............... 436/518 |
| 2002/0166962 A1 * | 11/2002 | Roukes et al. ............... 250/306 |
| 2003/0054355 A1 * | 3/2003 | Warthoe ........................ 435/6 |
| 2004/0132220 A1 * | 7/2004 | Fish ........................... 436/525 |
| 2005/0121615 A1 * | 6/2005 | Prater et al. ................. 250/343 |
| 2005/0133877 A1 * | 6/2005 | Thaysen et al. ............. 257/414 |
| 2005/0184746 A1 * | 8/2005 | Altmann et al. ............. 324/754 |
| 2006/0057026 A1 * | 3/2006 | Boiadjiev et al. ............. 422/88 |
| 2006/0191320 A1 * | 8/2006 | Pinnaduwage et al. ..... 73/24.06 |
| 2007/0237676 A1 * | 10/2007 | Colton et al. .............. 422/68.1 |

FOREIGN PATENT DOCUMENTS

| WO | WO 9938007 A1 * | 7/1999 |
| WO | WO 0014539 A1 * | 3/2000 |
| WO | WO 0133226 A1 * | 5/2001 |

(Continued)

OTHER PUBLICATIONS

Berger et al., "Surface Stress in the Self-Assembly of Alkanethiols on Gold", Jun. 27, 1997, Science Magazine, vol. 276, pp. 2021-2024.*

(Continued)

*Primary Examiner*—David A. Rogers (57) ABSTRACT

This invention relates to a microcantilever stress sensor for detecting and quantifying low levels of contaminants in liquids and gases. The invention uses a chemical agent to impart chemical specificity to the microcantilever stress sensor. The microcantilever deflects when the chemical agent is replaced by a more strongly adsorbing chemical species. The magnitude of the deflection is then used as a measure of the quantity of contaminant present.

18 Claims, 8 Drawing Sheets

FOREIGN PATENT DOCUMENTS

WO     WO 03104784 A1 * 12/2003

OTHER PUBLICATIONS

McKendry et al., "Multiple Label-Free Biodetection and Quantitative DNA-binding Assays on a Nanomechanical Cantilever Array", Jul. 23, 2002, Proceedings of the National Academy of Sciences, vol. 99, No. 15, pp. 9783-9788.*

"Attogram detection using nanoelectromechanical oscillators", B. Ilic et al., Journal of Applied. Physics, vol. 95, No. 3694 (Apr. 2004).*

"Virus detection using nanoelectromechanical devices", B. Ilic et al., Applied Physics Letters, vol. 85, No. 13 (Sep. 2004).*

"Study of intrinsic localized vibrational modes in micromechanical oscillator arrays", M. Sato et al., Chaos, vol. 13, No. 2 (Jun. 2003).*

A micromechanical flow sensor for microfluidic applications, D. A. Czaplewski et al., Journal oif Microelectromechanical Systems, vol. 13, No. 4 (Aug. 2004).*

"Nanodevices Target Viruses", B. Dume, available on the internet at <http://www.physicsworld.com>, Oct. 2004.*

"Cornell Researchers Move Beyond 'Nano' to 'Atto' to Build a Scale Sensitive Enough to Weigh a Virus", B. Steele, available on the internet at <http://www.news.cornell.com>, Apr. 2004.*

Nickolay V. Lavrik, et al., "Cantilever transducers as a platform for checmical and biological sensors", *Review of Scientific Instruments*, vol. 75, No. 7, Jul. 2004, 2229-2253.

European Search Report for Application EP 05024608, Oct. 16, 2009.

* cited by examiner

Chamber Side View

Side Elevation

Figure 2b

Chamber Top View

Top view

Figure 8

MICROCANTILEVER STRESS SENSOR FOR FLUID ANALYSIS

This application claims the benefit of U.S. Provisional application No. 60/628,282 filed Nov. 16, 2004.

FIELD OF THE INVENTION

The present invention is concerned with microcantilever stress sensors used to detect contaminants in fluids.

BACKGROUND OF INVENTION

Microcantilever sensors are known to be effective for detecting chemical substances at low levels. They can function in two ways. First microcantilevers function as resonators. In this mode, the microcantilever that is coated with a chemically sensitive material attracts a chemical species of interest. As mass adds to the microcantilever, its resonance frequency changes and the change in frequency can be used to quantify the added mass. Secondly, microcantilevers can be used as stress sensors. In this mode, microcantilevers are coated on one side with a chemically sensitive material to which the chemical species of interest adsorbs. When adsorption occurs it creates a chemical imbalance causing the cantilever to bend or deflect. The degree of microcantilever deflection can be used to quantify the concentration of the chemical species to which the microcantilever has been exposed. The present invention is concerned with microcantilever stress sensors that are used to detect contaminants in fluids. Fluid refers to both liquids and gases.

In addition to high sensitivity, a useful microcantilever sensor has to have chemical selectivity. It must be able to distinguish one chemical species from another. Typically, the materials used to sensitize microcantilever stress sensors can adsorb a variety of chemical species which cause the microcantilever to deflect. When used for detection in complex chemical mixtures it is not possible to determine what chemical has been detected.

There is a need to provide a microcantilever stress sensor for selectively detecting a preselected contaminant in a fluid.

There is also a need to provide a method for using a microcantilever stress sensor to determine the concentration of a contaminant in a fluid. In addition, there is a need to provide an array comprising a plurality of microcantilever stress sensors for detecting preselected contaminants in a fluid and determining their concentrations. Accordingly this invention and its embodiments can satisfy these needs.

SUMMARY OF INVENTION

The present invention relates to a microcantilever stress sensor, which is capable of selectively detecting a contaminant in a fluid in the presence of at least one other contaminant.

In one embodiment of the present invention is a microcantilever stress sensor for detecting a preselected contaminant in a fluid comprising:
  a flexible microcantilever adapted to be in contact with said fluid,
  a sensitizing layer on one side of said microcantilever,
  a chemical agent adsorbed on said sensitizing layer, said chemical agent capable of being preferentially displaced by said preselected contaminant when present in said fluid,
  a sensing means capable of detecting motion of said microcantilever.

In another embodiment of the present invention is a method for using a microcantilever stress sensor to quantify the concentration of a preselected contaminant in a fluid comprising:
  depositing on one surface of a microcantilever sensor a sensitizing layer,
  exposing said microcantilever sensor to a fluid,
  sensing the deflection of said microcantilever sensor,
  calculating the concentration of said preselected contaminant from the amount of deflection by using a calibration equation.

Yet another object of the invention is to provide an array of microcantilever stress sensors for detecting preselected contaminants in a fluid comprising:
  at least two flexible microcantilevers adapted to be in contact with said fluid,
  at least one sensitizing layer applied to one side of at least two of said microcantilevers,
  at least one chemical agent adsorbed to at least one of said sensitizing layers, said chemical agent capable of being preferentially displaced by a preselected contaminant when present in the fluid,
  a sensing means capable of detecting motion of said microcantilever.

DETAILED DESCRIPTION OF THE PREFERRED EMBODIMENTS

One embodiment of the present invention is to improve the ability of microcantilever stress sensors to discriminate between different chemical contaminants in a fluid. In this way the microcantilver stress sensor will be more effective in determining to which contaminant it has been exposed and be more useful as a chemically discriminating sensor.

In theory stress induced deflection can be observed with macroscopic cantilevers. However, sensitivity is substantially increased by making the cantilever small so that it is more sensitive to small stresses. The present invention involves microcantilevers, which are cantilevers, which have a length of less than 1000 micrometers, preferably less than 500 micrometers even more preferably less than 250 micrometers and a width of less than 100 micrometers, preferably less than 50 micrometers even more preferably less than 25 micrometers and a thickness of less than 10 micrometers, preferably less than 5 micrometers even more preferably less than 2.5 micrometers.

Figure 1A:
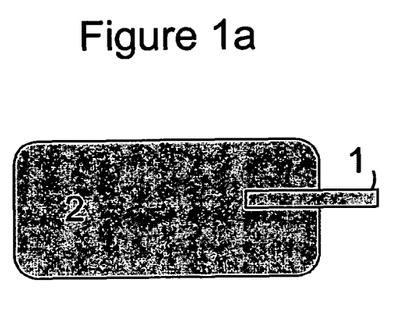
FIG. 1a is an illustration of a diving board microcantilever stress sensor attached to a substrate.
Figure 1B:
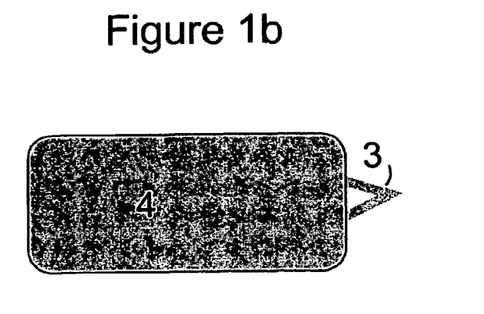
FIG. 1b is an illustration of a triangular microcantilever stress sensor attached to a substrate.

Various microcantilever geometries and shapes are available. Two non-limiting examples of microcantilever designs are depicted in FIGS. 1a and 1b. A diving board microcantilever 1 is shown in FIG. 1a attached to a substrate 2 and a triangular microcantilever 3 is shown in FIG. 1b attached to a substrate 4. They are often sold for use as sensors for atomic force microscopes (AFM).

Microcantilevers are generally attached to a rigid substrate as shown in FIGS. 1a and 1b. In general, the microcantilevers are produced and sold already attached to the rigid substrate. Typically, the microcantilever and substrate are lithographically produced from silicon.

Figure 2A:
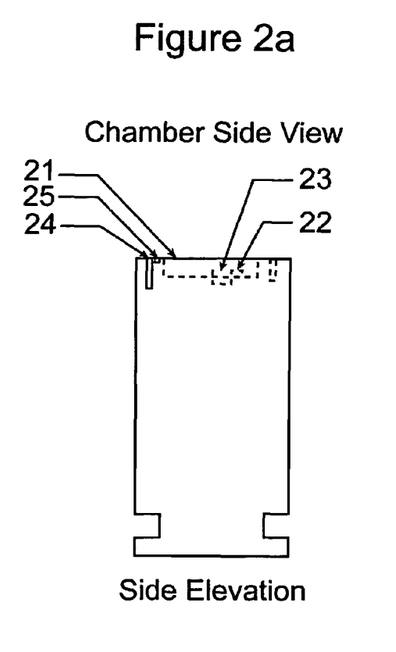
FIG. 2a is a side view illustration of a cell for holding fluid and microcantilever stress sensor.
Figure 2B:
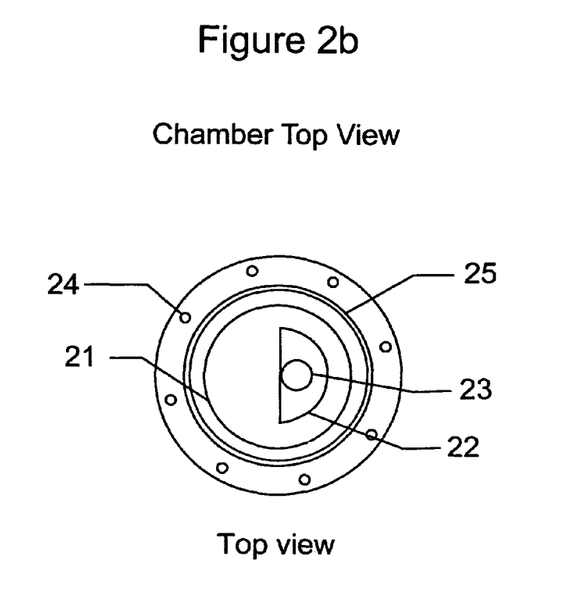
FIG. 2b is a top view illustration of a cell for holding fluid and microcantilever stress sensor.

The microcantilever and its substrate are mounted into a sample cell. A cell 21 is shown in FIGS. 2a and 2b which are a side elevation and top view respectively. The purpose of the sample cell 21 is to bring the microcantilever into contact with the fluid to be analyzed. In some cases it will be desirable to have a flow cell with an inlet and outlet for continues fluid analysis. In the non-limiting example depicted in FIGS. 2a and 2b, the microcantilever substrate is glued to an iron plate and secured to a pedestal 22 by a magnet 23 embedded in the cell. A transparent window may also be attached with screws that are screwed into threaded holes 24 in the top of the cell. An O-ring placed in groove 25 is used to seal the window.

Chemical sensitivity is imparted to the microcantilever by coating one surface with a sensitizing layer. Since the microcantilever is flat it has two primary surfaces that comprise most of the surface area. Only one of these surfaces is covered with the sensitizing layer. The edges of the microcantilever have relatively little surface area. The edges of the microcantilever, which contain a small part of the microcantilever surface area may or may not be coated with the sensitizing layer. A microcantilever stress sensor is defined as a microcantilever, which has a sensitizing layer applied to one of the primary surfaces. The material used for the sensitizing layer is chosen so that contaminants in the fluid will adsorb to it. Therefore, the Gibbs free energy of adsorption of the contaminant to the sensitizing layer must be negative. The sensitizing layer covers more than 50% of the microcantilever. The sensitizing layer can be made out of a variety of materials. Non-limiting examples of sensitizing layers are metals, glass, zinc oxide and polymers. Preferably, the sensitizing layer is a metal. More preferable are the metals, gold, platinum, cobalt, nickel, iron and silver. Most preferably, the sensitizing layer is gold.

The sensitizing layer will typically be less than 1000 nanometers thick, preferably less than 500 nanometers thick and most preferably less than 50 nanometers thick.

An objective of the present invention is to improve the ability of microcantilever stress sensors to discriminate between different contaminants in the fluid. In this way the microcantilver stress sensor will be more effective in determining to which contaminant it has been exposed and be more useful as a chemically discriminating sensor. This is accomplished by exposing the sensitizing layer to a chemical agent.

Once the sensitizing layer has been applied, the microcantilever is exposed to the chemical agent. The chemical agent is chosen so that it has sufficient affinity for the sensitizing layer so that it adsorbs to the sensitizing layer but will desorb and be replaced by the chemical contaminant of interest. In addition the chemical agent, upon adsorption to the sensitizing layer, induces a surface stress which causes the microcantilever to deflect. The chemical agent remains adsorbed to the sensitizing layer in the presence of other fluid contaminants but will desorb and be displaced by the specific target contaminant that is to be detected. Adsorption of the chemical agent will cause the cantilever to deflect and achieve an equilibrium starting point. In the presence of some fluid components the chemical agent will remain adsorbed to the sensitizing layer and the microcantilever will not deflect additionally. However, in the presence of the target contaminant with a greater affinity for the sensitizing layer, the chemical agent will desorb and be displaced by the target contaminant. In this case the cantilever will deflect significantly indicating the presence of the target contaminant. This is referred to as a positive deflection response. The response may be in the positive or negative direction. In the presence of other contaminants with less affinity for the sensitizing layer, the chemical agent will not desorb. This is referred to as a lack of deflection response.

The chemical agent must be capable of adsorbing to the sensitizing layer and then desorbing in the presence of the contaminant of interest. Therefore, the Gibbs free energy for adsorption of the chemical agent onto the sensitizing layer must be negative. The chemical agent can be a gas or liquid. It can be a solid delivered to the microcantilever by dissolving in a suitable liquid solvent. Preferably the chemical agent will have a formula weight between 25 and 750. More preferably the chemical agent will have a formula weight between 30 and 600 and contain at least two carbon atoms. Even more preferably the chemical agent will be selected from the group consisting of alkanes, alkenes, amines, alcohols, thiols, carboxylic acids and salts of carboxylic acids. Most preferably the chemical agent should be octadecene or oleic acid.

The chemical agent must have a negative Gibbs free energy of adsorption with the sensitizing layer. The suitability of a chemical agent for selectively detecting a preselected contaminant can be determined by comparing its Gibbs free energy of adsorption to the sensitizing layer with the Gibbs free energy of adsorption of a preselected contaminant and the sensitizing layer. The Gibbs free energy for the adsorption of the chemical agent to the sensitizing layer must be less negative than the Gibbs free energy for the adsorption of the contaminant of interest to the sensitizing layer. In this case the chemical agent will desorb from the sensitizing layer and be replaced by the contaminant of interest.

The ability of the microcantilever stress sensor to discriminate between two contaminants can be tuned by selecting an appropriate chemical agent. If the chemical agent has a Gibbs free energy of adsorption for the sensitizing layer which is between the Gibbs free energies of adsorption of the two contaminants with the sensitizing layer, then the microcantilever stress sensor will be able to discriminate between the two contaminants. Only the contaminant with a Gibbs free energy of adsorption that is more negative than that of the chemical agent will displace the chemical agent resulting in deflection of the microcantilever stress sensor.

In another embodiment of the present invention a microcantilever sensor can be used to determine the concentration of a target contaminant. This is done by measuring the distance deflected by the microcantilever stress sensor in response to the target contaminant. The microcantilever will deflect more in response to a higher concentration of target contaminant. At high concentration the microcantilever will achieve its maximum deflection limit beyond which no additional deflection will occur.

In order to determine absolute contaminant concentration from the amount of microcantilever sensor deflection it is desirable to develop a calibration curve. This is achieved by calibrating the distance deflected by the microcantilever sensor to the concentration of contaminant using calibration solutions with known concentrations of the target contaminant. A deflection vs. concentration calibration curve is then plotted. The data points are then fit to a mathematical function and the functional constants are calculated from the best least-squares fit. There are many computerized mathematical software packages that do this adequately. A calibration equation is the mathematical function including the calculated functional constants. A similar microcantilever stress sensor with the same sensitizing layer and the same chemical agent used to develop the calibration curve can then be exposed to a fluid containing an unknown concentration of the target contaminant. The distance deflected can be used with the calibration equation to calculate the concentration of the target contaminant.

The mathematical function applied to the measured calibration data is preferably based on the following equation:

$$\text{Cantilever deflection}/M = 100\, KC/[1+KC] \quad (1)$$

where C is the concentration or mole fraction of the target contaminant, K is the equilibrium constant derived from a fit of the experimental calibration data and M is the maximum distance deflected by the microcantilever at high concentration. M and K are calculated for a target contaminant for a given microcantilever sensor type prepared with a sensitizing layer and a chemical agent. A similarly prepared microcantilever sensor can then be used to determine C, concentration of a target contaminant, from a measured cantilever deflection.

Figure 3:
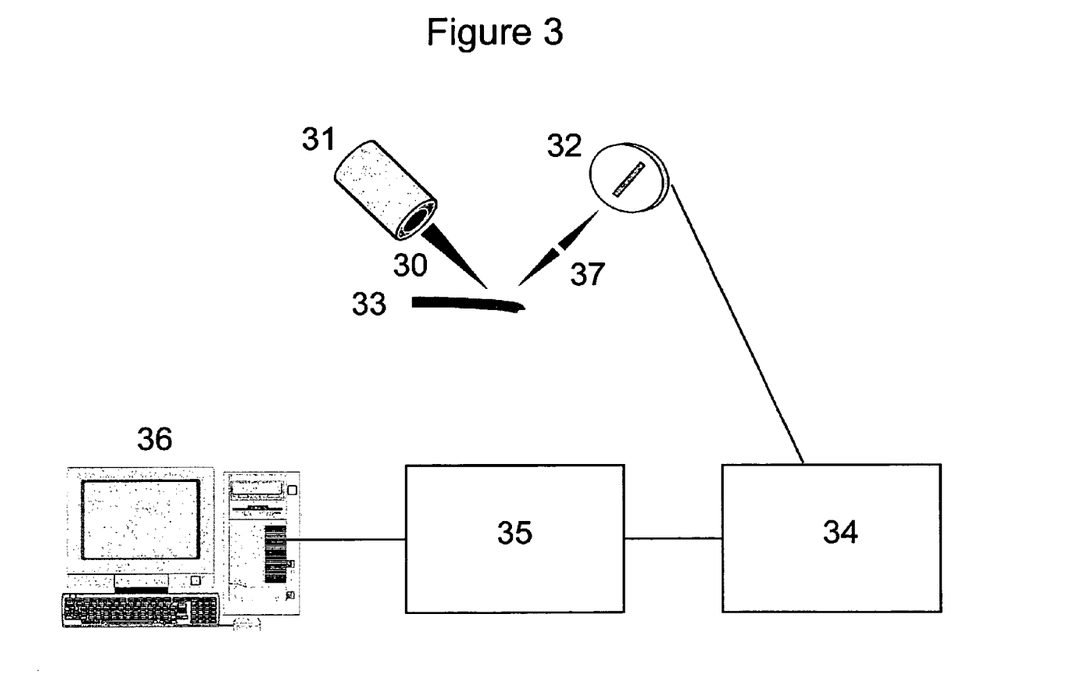
FIG. 3 is an illustration of an optical beam deflection detector for sensing deflection of a microcantilever stress sensor.

The distance traveled by the deflecting microcantilever can be determined by various means. One common method is depicted in FIG. 3. A laser beam 30 from a laser source 31 is focused onto a microcantilever 33. The reflected laser beam 37 is than directed onto a Position Sensitive Detector (PSD) 32. Suitable PSDs are available from a number of commercial sources. The voltage output from the PSD electronic circuitry 34 board is directed to a signal conditioning amplifier 35 and digitized and stored on a laboratory computer data acquisition system 36.

Alternative methods for detecting cantilever motion are possible. For example, microcantilevers can be manufactured with embedded strips such as piezoelectric or piezoresistive materials. In this case the microcantilever directly generates an electrical signal which varies depending on the amount of deflection.

Figure 4:
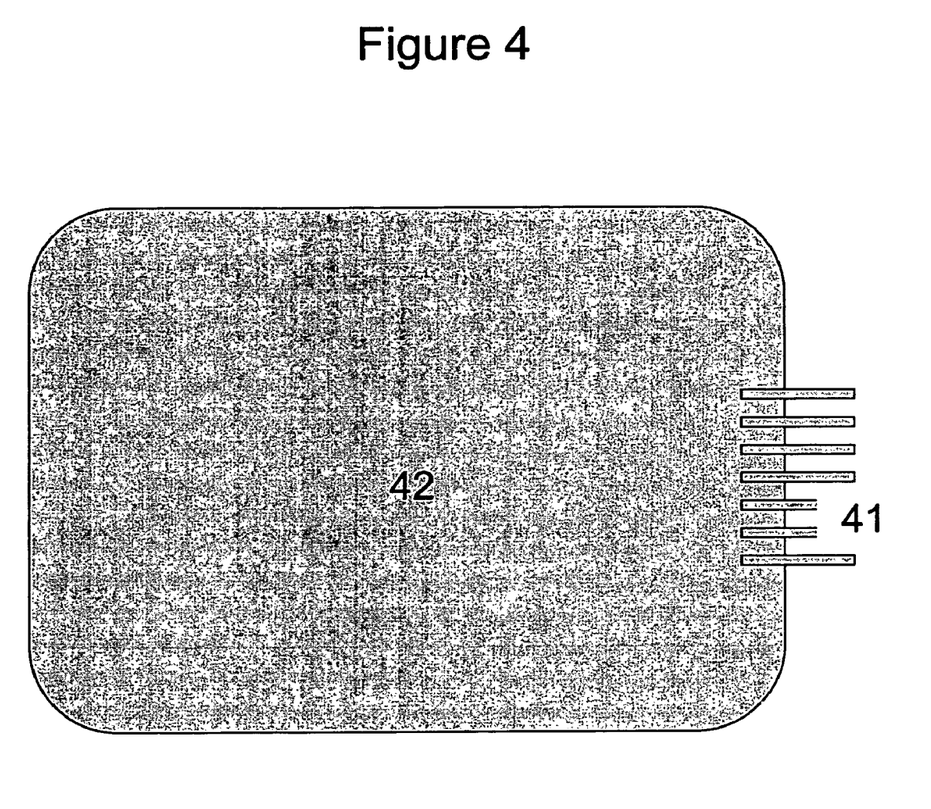
FIG. 4 is an illustration of a cantilever array.

A preferred embodiment of the invention is an array comprising a plurality of microcantilevers each with a sensitizing layer and a chemical agent on one surface. This enables improved reliability and sensitivity and also enables detection of multiple target contaminants. For example, if one set of microcantilevers in the array is covered on one surface with a sensitizing layer and exposed to a chemical agent and a different set of microcantilevers in the same array is covered on one surface with a sensitizing layer and exposed to a different chemical agent, contaminant A might cause a deflection response in one set of microcantilevers while contaminant B might cause a deflection response in the other set of microcantilevers. One could create a large array with hundreds of microcantilevers coated with different combinations of sensitizing layers and chemical agents. This would allow one to detect and differentiate many different target contaminants by monitoring cantilever deflection patterns. A diagram of a cantilever array is shown in FIG. 4 where multiple cantilevers 41 are attached to a common cantilever substrate 42.

An especially preferred embodiment of the invention is an array of microcantilevers comprising at least two microcantilevers. Each microcantilever is covered on one side with a sensitizing layer. At least one—but not all—of the sensitizing layers is further covered with a chemical agent. This latter microcantilever which has been exposed to the chemical agent is used to positively identify the target contaminant. This is accomplished by measuring the deflection response of the microcantilever. The former microcantilever with only a sensitizing layer is used to determine the concentration of the target contaminant. This is accomplished by measuring the distance deflected by the microcantilever and using a calibration equation to convert distance deflected into concentration.

Various mathematical methods may be used to determine the identity of a target contaminant when an array containing large numbers of microcantilevers is employed. For example, an array of microcantilevers treated with various sensitizing layers and chemical agents can be exposed to a reference fluid containing a specific target contaminant at a known concentration. In this case the microcantilevers in the array will produce a specific deflection pattern because microcantilevers with different sensitizing layers and different chemical agents will deflect in different amounts in response to the target contaminant. Identically prepared microcantilever arrays can be exposed to reference fluids with other known target contaminants at known concentrations. The array will have a unique deflection pattern response for each target contaminant. These calibration deflection pattern data, developed with reference fluids containing known target contaminants at known concentrations can than be analyzed to develop rules for predicting the deflection pattern which will occur for a specific target contaminant or combination of contaminants. A preferred method for analyzing the deflection patterns is using neural net analysis.

In many cases it will be useful to include a reference microcantilever in the array to account for spurious temperature noise and drift. For example, a chemically inert microcantilever is used to monitor deflection due to temperature or fluid flow. These effects are then subtracted or divided out of the deflection responses of the chemically sensitive microcantilevers.

EXAMPLES

Example 1

Figure 5:
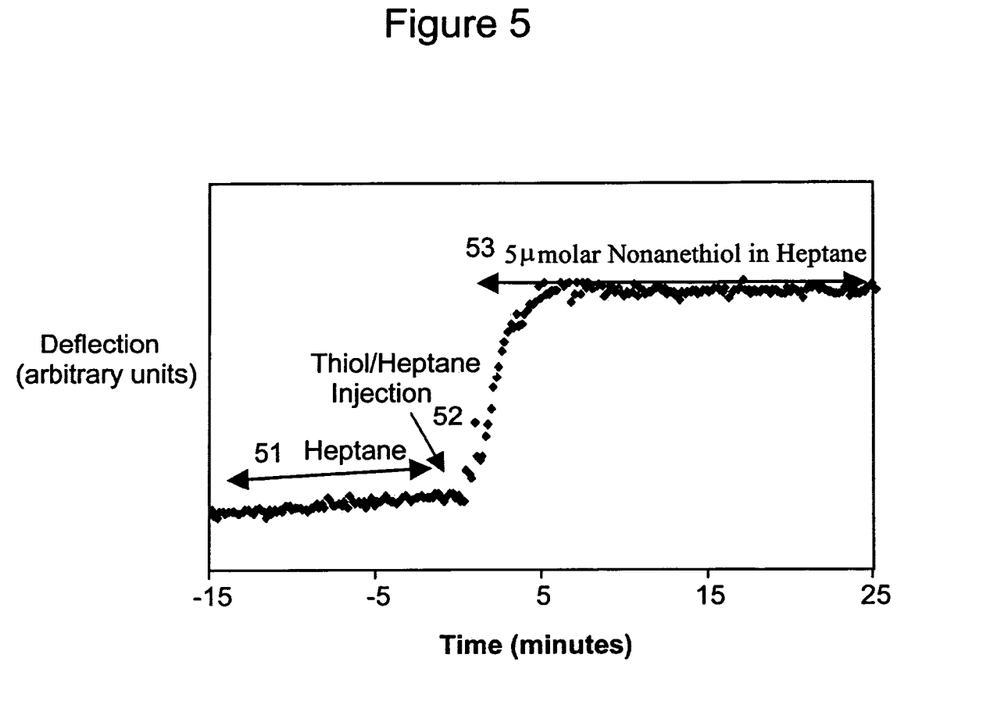
FIG. 5 is a set of experimental data showing response of gold-coated microcantilever stress sensor to 1-nonanethiol.

An uncoated silicon microcantilever (Budget Cantilevers Model BS-Cont) was placed in a vapor deposition chamber and covered, on one side, with an approximately 25 nanometer thick coating of gold. The microcantilever was than placed inside a 3.5 milliliter cell which was covered with a transparent quartz window. Normal heptane was injected into the cell and a flow of 2 microliters per minute was maintained. Microcantilever deflection was measured using the optical beam deflection method. The output of a small diode laser (Oz Optics) with an output wavelength of 670 nanometers was focused onto the cantilever and the reflection was directed onto the active element of a Hammamatsu model S3979 position sensitive detector. Data were amplified with a Stanford Research Model 560 preamplifier and acquired in a PC based laboratory data acquisition system. After a stable baseline was achieved in n-heptane a solution of 1-nonanethiol dissolved in n-heptane (5 micromolar concentration) was injected into the cell. After an initial rapid injection of 16 milliliters the 1-nonanethiol solution was flowed at 2 microliters per minute. Data are shown in FIG. 5. The initial flat part of the data trace was generated in n-heptane 51. Arrow 52 indicates the injection of 5 micromolar solution of 1-nonanethiol dissolved in n-heptane. It is readily apparent that the cantilever deflected when the 1-nonanethiol solution was injected and the deflection reached a maximum after injection as shown by region 53.

Example 2

Figure 6:
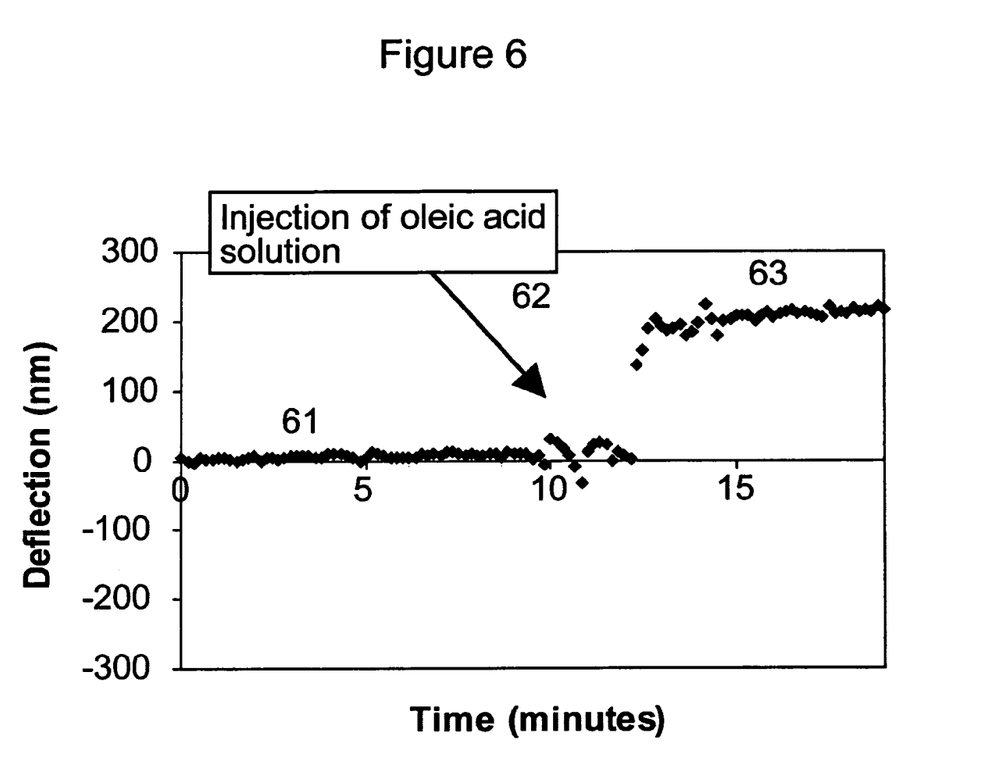
FIG. 6 is a set of experimental data showing response of gold-coated microcantilever stress sensor to oleic acid.

An uncoated silicon microcantilever (Budget Cantilevers Model BS-Cont) was placed in a vapor deposition chamber and covered, on one side, with an approximately 25 nanometer thick coating of gold. The microcantilever was than placed inside a 3.5 milliliter cell which was covered with a transparent quartz window. Normal heptane was injected into the cell and a flow of 2 microliters per minute was maintained. Microcantilever deflection was measured using the optical beam deflection method. The output of a small diode laser (Oz Optics) with an output wavelength of 670 nanometers was focused onto the cantilever and the reflection was directed onto the active element of a Hammamatsu model S3979 position sensitive detector. Data were amplified with a Stanford Research Model 560 preamplifier and acquired in a PC based laboratory data acquisition system. After a stable baseline was achieved in n-heptane a solution of oleic acid dissolved in n-heptane (0.0013 molar concentration) was injected into the cell. After an initial rapid injection of 16 milliliters the oleic acid solution was flowed at 2 microliters per minute. Data are shown in FIG. 6. The initial flat part of the data trace was generated in n-heptane 61. Arrow 62 indicates the injection of 0.0013 molar solution of oleic acid dissolved in n-heptane. It is readily apparent that the cantilever deflected when the oleic acid solution was injected and deflection reached a maximum after the injection as shown by region 63.

A comparison of the deflection data shown in FIGS. 5 and 6 indicate that the microcantilever covered in a gold sensitizing layer deflects in response to both oleic acid and 1-nonanethiol. Consequently, the microcantilever coated on one side with gold does not discriminate between the presence of oleic acid and the presence of 1-nonanethiol.

Example 3

An uncoated silicon microcantilever (Budget Cantilevers Model BS-Cont) was placed in a vapor deposition chamber and covered, on one side, with an approximately 25 nanometer thick coating of gold. The microcantilever was than placed inside a 3.5 milliliter cell which was covered with a transparent quartz window. The cell was filled with n-heptane and the output of a small diode laser (Oz Optics) with an output wavelength of 670 nanometers was focused onto the cantilever and the reflection was directed onto the active element of a Hammamatsu model S3979 position sensitive detector. Data were amplified with a Stanford Research Model 560 preamplifier and acquired in a PC based laboratory data acquisition system. The gold-coated microcantilever was exposed to a 0.0013 molar solution of oleic acid dissolved in n-heptane. In this case the gold coating serves as the sensitizing layer and oleic acid serves as the chemical agent which has adsorbed to the gold. The graph in FIG. 7, which starts after the microcantilever has been exposed to the oleic acid, shows the experimental deflection data trace for this microcantilever stress sensor. Initially (from time zero until about 7 minutes) n-heptane was flowed through the cell and no apparent deflection occurs 71. A 0.003 molar solution of 1-nonanethiol dissolved in n-heptane was than injected into the cell and is indicated in the figure by arrow 73. The data in FIG. 7 demonstrate that 1-nonanethiol caused the cantilever to deflect in the negative direction indicating desorption of the chemical agent which in this case is oleic acid. This is followed by deflection of the microcantilever in the positive direction indicating adsorption of 1-nonanethiol to gold as shown as region 74.

Figure 7:
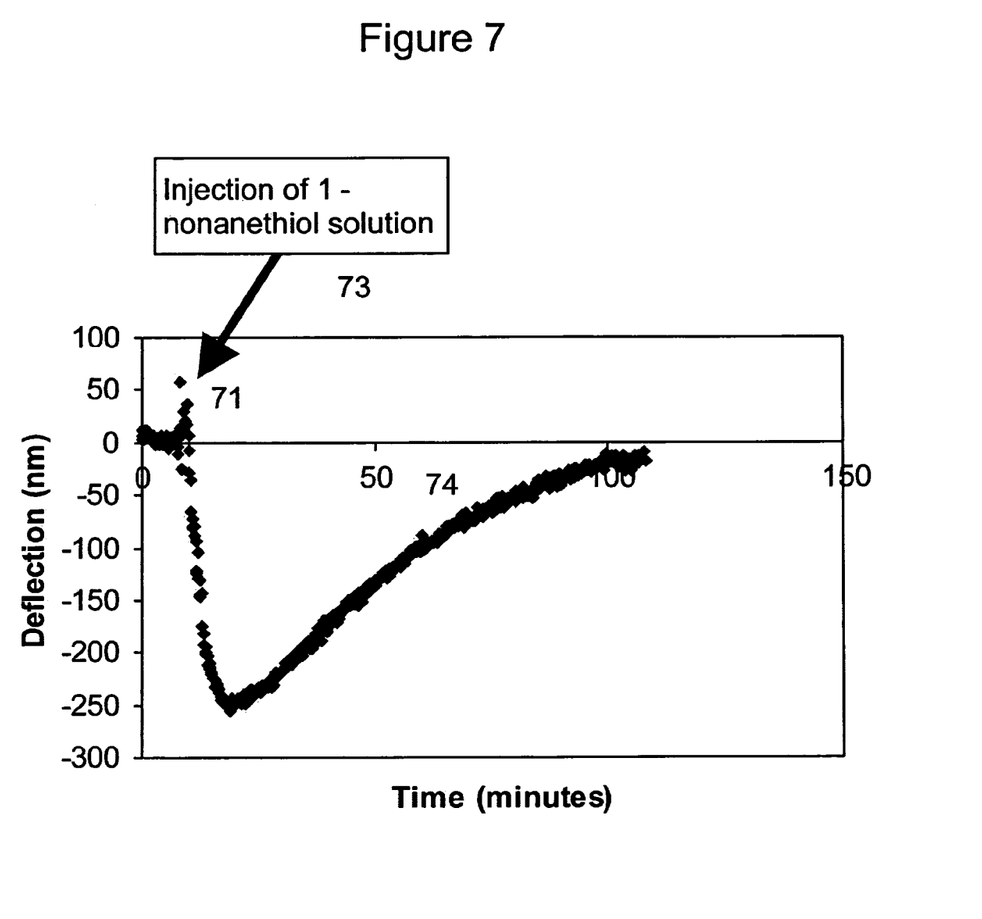
FIG. 7 is a set of experimental data showing response of gold-coated microcantilever, which has been treated with oleic acid to 1-nonanethiol.

It is apparent from the data in FIG. 7 that use of oleic acid as a chemical agent imparts chemical selectivity to the microcantilever. Only analytes which have a stronger affinity for gold than oleic acid—for example 1-nonanethiol—will cause the cantilever to deflect. The cantilever, prepared in this way, does not deflect upon exposure to oleic acid. Consequently, use of oleic acid as a chemical agent allows the microcantilever to discriminate between the presence of oleic acid and 1-nonanethiol.

Example 4

Figure 8:
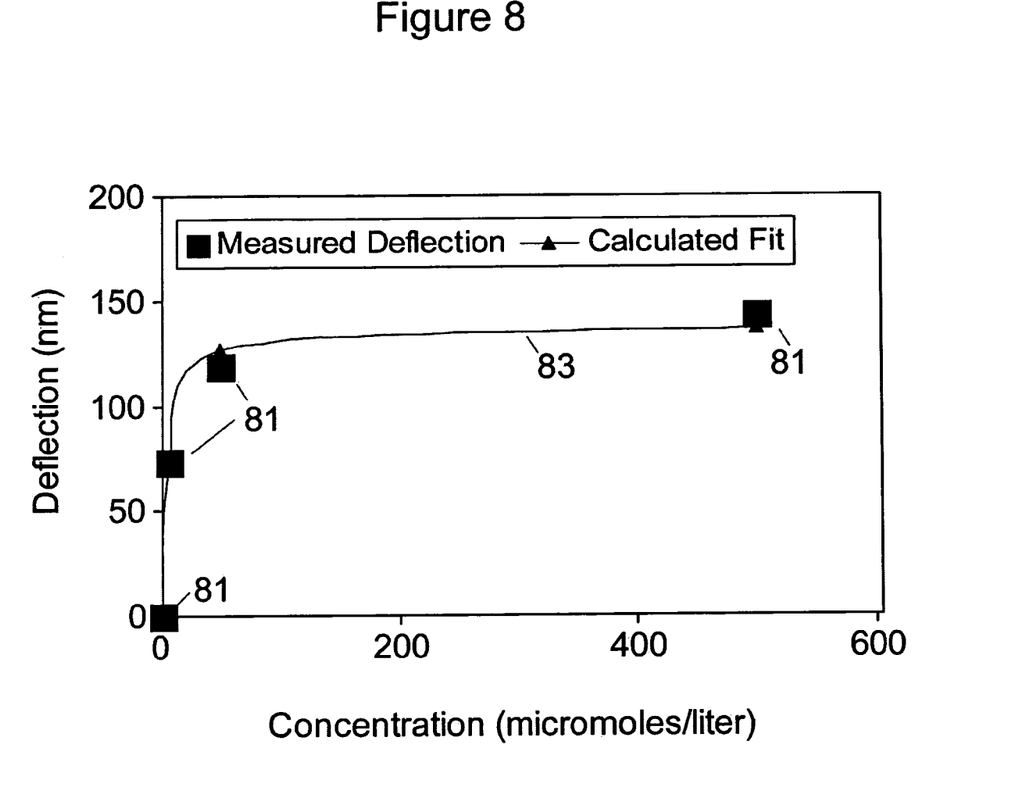
FIG. 8 is a set of experimental data showing deflection response of a gold-coated cantilever to different concentrations of 1-nonanethiol.

The concentration of a target contaminant can be predicted from the distance deflected by the microcantilever. An uncoated silicon microcantilever (Budget Cantilevers Model BS-Cont) was placed in a vapor deposition chamber and covered, on one side, with an approximately 25 nanometer thick coating of gold. The microcantilever was than cleaned inside a plasma cleaner and placed inside a 3.5 milliliter cell and covered with a transparent quartz window. Normal heptane was injected into the cell and a flow of 2 microliters per minute was maintained. The output of a small diode laser (Oz Optics) with an output wavelength of 670 nanometers was focused onto the cantilever and the reflection was directed onto the active element of a Hammamatsu model S3979 position sensitive detector. Data were amplified with a Stanford Research Model 560 preamplifier and acquired in a PC based laboratory data acquisition system. Three different amounts of 1-nonanethiol were dissolved in n-heptane. The three solutions had concentrations of 5, 50 and 500 micromolar, respectively. As shown in FIG. 8, these solutions were injected consecutively into the cell, deflections were measured 81 and a calculated fit determined 83. The microcantilever deflected more with increasing 1-nonanethiol concentration.

Equation 1 was fit to the experimental data points shown in FIG. 8 and the predicted line is represented by the solid line. The calculated values of M and K are 138 nm and 215000, respectively. K represents the equilibrium constant for adsorption of 1-nonanethiol on the plasma cleaned gold surface. This equilibrium constant represents a Gibbs free energy of −7.2 kcal/mol.

What is claimed is:

1. A microcantilever stress sensor for detecting a contaminant in a fluid comprising:
    a) a flexible microcantilever adapted to be in contact with the fluid, inside a flow cell with an inlet and outlet for continuous fluid analysis and a transparent window attached to the flow cell,
    b) a sensitizing layer on one side of the microcantilever,
    c) a chemical agent adsorbed on the sensitizing layer on only one side of the microcantilever, the chemical agent capable of being preferentially displaced by the preselected contaminant when present in the fluid by desorbing in the presence of the contaminant,
    d) a sensor capable of detecting motion of the microcantilever caused by desorption of the chemical agent and adsorption of the contaminant.

2. The microcantilever stress sensor of claim 1 wherein the chemical agent's Gibbs free energy for adsorption of the chemical agent onto the sensitizing layer is negative.

3. The microcantilever stress sensor of claim 1 further comprising a computer data acquisition system capable of showing desorption of the chemical and adsorption of the contaminant.

4. The microcantilever stress sensor of claim 1 wherein the chemical agent has a molecular weight between 25 and 750.

5. The microcantilever stress sensor of claim 4 wherein the chemical agent is selected from the group consisting of alkanes, alkenes, amines, alcohols, thiols, carboxylic acids, salts of carboxylic acids and any combination thereof.

6. The microcantilever stress sensor of claim 1 wherein the sensitizing layer is a metal.

7. The microcantilever stress sensor of claim 6 wherein the chemical agent is oleic acid.

8. The microcantilever stress sensor of claim 1 including:
   a) at least two flexible microcantilevers adapted to be in contact with the fluid, inside a flow cell with an inlet and outlet for continuous fluid analysis and a transparent window attached to the flow cell,
   b) at least one sensitizing layer applied to one side of at least two of the microcantilevers,
   c) at least one chemical agent adsorbed to at least one of the sensitizing layers on only one side of the microcantilever, the chemical agent capable of being preferentially displaced by a contaminant when present in the fluid,
   d) a sensing means capable of detecting motion of the microcantilevers.

9. The microcantilever stress sensor of claim 8 wherein the sensitizing layers are metals.

10. The microcantilever stress sensor at claim 8 further comprising a computer data acquisition system capable of showing desorption of the chemical and adsorption of the contaminant.

11. The microcantilever stress sensor of claim 8 wherein the chemical agent has a molecular weight between 25 and 750.

12. The microcantilever stress sensor of claim 11 wherein the chemical agent is selected from the group consisting of alkanes, alkenes, amines, alcohols, thiols, carboxylic acids combination thereof, salts of carboxylic acids and any combination thereof.

13. A method for using a microcantilever stress sensor to determine the concentration of a contaminant in a fluid comprising,
   depositing on one surface of a microcantilever sensor a sensitizing layer,
   exposing the microcantilever sensor with sensitizing layer to a chemical agent which adsorbs to the sensitizing layer, and which is capable of being preferentially displaced by the contaminant;
   exposing the microcantilever sensor to the fluid,
   sensing amount of deflection of the microcantilever sensor,
   calculating the concentration of the contaminant from the amount of deflection by using a calibration equation, amount of deflection/M=100 KC/[1+KC],
where C is the concentration of said contaminant and K and C are numbers greater than or equal to zero.

14. The method of claim 13 wherein the sensitizing layer is a metal.

15. The method of claim 13 wherein the chemical agent has a molecular weight between 25 and 750.

16. The method of claim 15 wherein the chemical agent is selected from the group consisting of alkanes, alkenes, amines, alcohols, thiols, carboxylic acids thereof, salts of carboxylic acids and any combination.

17. A method of using the microcantilever stress sensor of claim 1 wherein the contaminant is an alkylthiol, the fluid is a distillate fuel, and the sensitizing layer is a metal.

18. The method of claim 17 wherein the metal is gold and the chemical agent is oleic acid.

* * * * *